United States Patent [19]
Mogford

[11] 3,984,489
[45] Oct. 5, 1976

[54] STABILIZATION OF VINYLIDENE CHLORIDE DURING MANUFACTURING AND PURIFICATION

[75] Inventor: Riley F. Mogford, Angleton, Tex.

[73] Assignee: The Dow Chemical Company, Midland, Mich.

[22] Filed: June 25, 1975

[21] Appl. No.: 590,000

Related U.S. Application Data

[63] Continuation-in-part of Ser. No. 482,390, June 24, 1974, abandoned.

[52] U.S. Cl. .................. 260/654 D; 260/652.5 P
[51] Int. Cl.² ................ C07C 21/08; C07C 21/42
[58] Field of Search ............ 260/652.5 P, 652.5 R, 260/654 D

[56] References Cited
UNITED STATES PATENTS 2,160,944   6/1939   Coleman et al. ............ 260/652.5 P

FOREIGN PATENTS OR APPLICATIONS 619,758   3/1949   United Kingdom .......... 260/652.5 P
627,930   8/1949   United Kingdom .......... 260/652.5 P

*Primary Examiner*—D. Horwitz
*Attorney, Agent, or Firm*—A. Cooper Ancona

[57] ABSTRACT

A method for preventing the polymerization of vinylidene chloride (1,1-dichloroethylene) during the manufacture thereof by the caustic dehyrochlorination at elevated temperatures of crude 1,1,2-trichloroethane which comprises admixing and maintaining in intimate association with the reaction mixture and its reaction products from about 50 to about 1500 ppm by weight of an amine having a boiling point between about 50°C and 160°C.

5 Claims, No Drawings

STABILIZATION OF VINYLIDENE CHLORIDE DURING MANUFACTURING AND PURIFICATION

CROSS REFERENCE TO RELATED APPLICATION

This is a continuation-in-part of my copending application Ser. No. 482,390 filed June 24, 1974 and now abandoned.

BACKGROUND OF THE INVENTION

In the manufacture of vinylidene chloride (1,1-dichloroethylene) by the dehydrohalogenation at elevated temperatures of 1,1,2-trichloroethane in the presence of caustic, the unsaturated vinylidene chloride product is very likely to polymerize either in the reactor or in the purification system thereafter because of conditions which are conducive to polymer formation in both places. Thus, it becomes necessary to employ some compound which will inhibit the polymerization.

Amines generally have been employed as stabilizers and storage inhibitors at ambient temperatures for chlorinated hydrocarbons, especially for inhibiting the polymerization reaction of the unsaturated chlorinated hydrocarbons such as vinyl chloride, vinylidene chloride, trichloroethylene and the like. Light and air are catalysts for the polymerization of such compounds and lower alkyl amines and aromatic amines have been claimed to protect vinylidene chloride in storage (U.S. Pat. No. 2,160,944). Isopropylamine is claimed in British patent 627,930 as an inhibitor for vinylidene chloride in the presence of air at elevated temperatures (65° C).

Phenols have been employed as storage stabilizers for trichloroethylene and other chlorinated hydrocarbons either alone or in combination with substituted phenols and other compounds. Such stabilizers are disclosed in U.S. Pat. Nos. 3,230,175; 3,293,312 and 3,767,507.

Such compounds cannot be employed in the dehydrochlorination reactor, however, for, if they contact the caustic, they will react with it and be lost as inhibitors. Further, the phenolic compounds may even inhibit the dehydrohalogenation reaction. Thus, the usual way to employ phenolic inhibitors is to add them to the condenser immediately following the reactor. The inhibitor must also be carried over into the drying and finishing columns, or added thereto, in order to prevent polymerization there also. These inhibitors (phenolic compounds) will not pass overhead with the vinylidene chloride, but remain with the unreacted beta-trichloroethane. Before the unreacted starting material can be recycled to the reactor, it must be separated from such phenolic inhibitors for the reasons given heretofore.

Thus, it would be desirable to have an inhibitor which would not be deleterious to the reaction, nor be lost by reaction with caustic, which could be carried through the drying step to the distillation column and could be recycled to the reactor with the unreacted beta-trichloroethane.

BRIEF DESCRIPTION OF THE INVENTION

It has now been found in accordance with the present invention that the maintenance in the overhead of the reactor of from 50 to about 1500 ppm by weight of an amine having a boiling point between about 50° C and about 160° C, such as for example, a dialkylamine, particularly di-n-propylamine, will prevent the polymerization of vinylidene chloride in the reactor following its formation by a dehydrochlorination reaction as well as preventing its polymerization during drying and purification by distillation following its production.

It is a particular advantage of this invention that an inhibitor, or stabilizer, such as di-n-propylamine, will not be lost from the system and is recyclable back to the reactor for continued protection of the entire system. It is of course understood that very small quantities will be lost with the water out of the bottom of the reactor and drying column, but the major portion of the stabilizer remains with the reactor effluent through the drying step and is carried through to the distillation column from whence it is returned to the dehydrochlorination reactor along with the beta-trichloroethane and other recyclable materials.

DETAILED DESCRIPTION OF THE INVENTION

In accordance with the present invention beta-trichloroethane (1,1,2-trichloroethane) is contacted with sodium hydroxide at a temperature of from about 90° C to about 120° C to effectuate its dehydrohalogenation to 1,1-dichloroethylene. When one introduces into this reactor along with the 1,1,2-trichloroethane an amine having a boiling point between about 50° and 160° C, e.g., di-n-propylamine, there is obtained the beneficial effect that the vinylidene chloride produced by the dehydrochlorination is not subject to polymerization steps which follow its formation. It is found that a major proportion of the amine introduced into the reactor is returned in the recycle stream to the reactor with the unreacted beta-trichloroethane from the finishing still bottoms.

The conventional still for the removal of the beta-trichloroethane from the still bottoms of the finishing column to eliminate the conventional phenol stabilizer is not required. The amine does not react with the caustic as does a phenolic-type inhibitor and can be recycled to the reactor. Thus, when one employs the stabilizer of the present invention, a definite advantage is provided the overall process by eliminating a process step and a piece of equipment, i.e., the distillation column to remove inhibitor.

Compounds useful as inhibitors and having boiling points within the range indicated (50°–160° C) are those having the formula

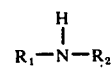

wherein $R_1$ and $R_2$ are independently selected from the group of alkyl radicals having from 1 to 4 carbon atoms.

Thus, representative compounds having the above formula are diethylamine, ethyl-n-propylamine, di-n-propylamine, diisopropylamine, methyl-n-propylamine, di-n-butylamine, diisobutylamine, ethyl-n-butylamine, and the like. The amount employed is preferably 200–500 ppm based on the total chlorinated hydrocarbons present. As little as 50 or as much as 1500 ppm can be effectively employed however.

The dehydrochlorination is generally conducted at a temperature of about 95° C at a pressure of about 25 psig. This temperature of course will vary depending upon the pressure and the composition of the reaction mixture. Thus, temperatures within the range of from about 90° to about 120° C and pressures of from about 15–35 psig are employed for the dehydrochlorination of the 1,1,2-trichloroethane.

In a representative example an aqueous solution of sodium hydroxide was introduced into the bottom of a reactor at a rate of 112.0 moles/hr. and intimately admixed therein with a stream of 1,1,2-trichloroethane simultaneously introduced at a rate of 108.6 moles/hr. The temperatures in the reactor was maintained at about 100° C. A polymerization inhibitor (di-n-propylamine) was added so as to provide 0.036 moles/hr. in the overhead effluent which also contained 107.9 moles/hr. 1,1-dichloroethylene, 0.65 moles/hr. lights, 26.9 moles/hr. 1,1,2-trichloroethane and 59.2 moles/hr. water. Water, small amounts of caustic and sodium chloride were taken off the bottom of the reactor. The overhead effluent from the reactor was passed to a drying column where most of the water was removed. The product 1,1-dichloroethylene was then taken overhead in a distillation column and the unconverted 1,1,2-trichloroethane taken out of the bottom and thence to a stripper column to remove lights prior to recycling to the reactor. Small amounts of the di-n-propylamine were lost with the water removed from the bottom of the reactor and from the drying column. Thus, only small amounts of makeup inhibitor were required on an intermittent basis to maintain a level of about 250 ppm in the overhead effluent of the reactor. Pressure in the reactor and drying column was maintained at about 25 psig, while only about 5–15 psig was employed in the vinylidene chloride still and stripper columns in the remainder of the system.

I claim:

1. In a process for the manufacture of vinylidene chloride by the dehydrohalogenation of beta-trichloroethane in the presence of caustic at a reaction temperature in the range of about 90° to 120° C wherein a polymerization inhibitor is employed, the improvement consisting essentially of adding to the reaction mixture an amount of from about 50 to 1500 ppm based on the beta-trichloroethane of an inhibitor having the formula

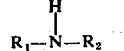

wherein $R_1$ and $R_2$ are alkyl radicals independently selected from the group of alkyl radicals having from 1 to 4 carbon atoms.

2. The process of claim 1 wherein the lower dialkylamine has a boiling point at atmospheric pressure of from about 50° to about 160° C.

3. A method for preventing the polymerization of vinylidene chloride during the production thereof by the caustic dehydrochlorination of crude 1,1,2-trichloroethane at a reaction temperature in the range of about 90° C to 120° C which comprises admixing and maintaining in the reactor and purification columns from about 50 to about 1500 ppm of a lower dialkylamine having the formula

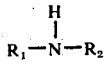

wherein $R_1$ and $R_2$ are alkyl radicals independently selected from the group of alkyl radicals having from 1 to 4 carbon atoms, said parts of amine being based on the total parts by weight of chlorinated hydrocarbons present.

4. The process of claim 3 wherein the lower dialkylamine has a boiling point at atmospheric pressure of from about 50° C to about 160° C.

5. The process of claim 3 wherein part of the amine is provided in a recycle stream containing unreacted 1,1,2-trichloroethane.

* * * * *